(12) United States Patent
Hara et al.

(10) Patent No.: US 6,417,881 B1
(45) Date of Patent: Jul. 9, 2002

(54) IMAGE ROTATING DEVICE OF STOMATOCAMERA

(75) Inventors: Kazuaki Hara; Terumi Takemoto; Shigeo Tamura, all of Tokyo (JP)

(73) Assignee: The Yoshida Dental Mfg. Co., Ltd. (JP)

(*) Notice: Subject to any disclaimer, the term of this patent is extended or adjusted under 35 U.S.C. 154(b) by 0 days.

(21) Appl. No.: 09/174,840

(22) Filed: Oct. 19, 1998

(30) Foreign Application Priority Data

Oct. 17, 1997 (JP) .............................................. 9-285147

(51) Int. Cl.[7] .............................. H04N 7/18; A62B 1/04
(52) U.S. Cl. ............................................. 348/66; 433/55
(58) Field of Search ................................. 348/66, 63, 65, 348/77, 82, 85, 68; 433/29, 55, 215; 600/167, 432; 359/425, 823, 894, 223, 226, 211; 128/903

(56) References Cited

U.S. PATENT DOCUMENTS

| | | | | |
|---|---|---|---|---|
| 4,775,887 A | * | 10/1988 | Tachi | 348/77 |
| 5,115,307 A | * | 5/1992 | Cooper et al. | 38/66 |
| 5,527,261 A | * | 6/1996 | Monroe et al. | 348/77 |
| 5,528,432 A | * | 6/1996 | Donahoo | 348/66 |
| 5,645,740 A | * | 7/1997 | Naiman et al. | 359/223 |
| 5,745,165 A | * | 4/1998 | Astuta et al. | 348/66 |

FOREIGN PATENT DOCUMENTS

| | | |
|---|---|---|
| JP | 63-133202 | 8/1988 |
| JP | 63-133203 | 8/1988 |
| JP | 63-133204 | 8/1988 |
| JP | 2-109554 | 4/1990 |
| JP | 5-111497 | 5/1993 |
| JP | 7-38846 | 5/1995 |

* cited by examiner

Primary Examiner—Chris Kelley
Assistant Examiner—Gims Philippe
(74) Attorney, Agent, or Firm—Ostrolenk, Faber, Gerb & Soffen, LLP

(57) ABSTRACT

Cylindrical support 20 having dope prism 2 built therein is rotatably fitted in barrel 23 as a constituent of stomatocamera frame 11. The support 20 has pin 22 erected on its periphery, and the barrel 23 is furnished with guide channel 4 formed along its circumference. The pin 22 pierces the guide channel 4 and protrudes from the periphery of the barrel 23. Protrudent end of the pin 22 is locked to locking channel 6 of operating ring 5 fitted to the periphery of the barrel 23. The dope prism 2 built in the camera frame is rotated by revolving the operating ring 5. Thus, the image can be rotated without the need to revolve the CCD camera frame.

8 Claims, 5 Drawing Sheets

IMAGE ROTATING DEVICE OF STOMATOCAMERA

BACKGROUND OF THE INVENTION

1. Field of the Invention

The present invention relates to a dental stomatocamera for displaying an image observed in the mouth on a TV monitor and relates particularly to an image rotating device capable of rotating an observed image and displaying it on a TV monitor.

2. Discussion of Related Art

Referring to FIG. 12, the conventional stomatocamera for photographing the condition inside the mouth comprises camera frame 11 fitted with built-in charge coupled device (CCD) 15 and, rotatably coupled therewith by means of coupler 17, lens unit 12 fitted with built-in prism 13 for introducing incident light and built-in fiber 14. Light is rotated by rotating the camera frame 11 by means of the coupler 17. The rotated light is subjected to photoelectric transfer and passed through control unit 18, and rotated image is displayed on TV monitor 19.

However, the rotating of the camera frame 11 in order to rotate an image as in the conventional stomatocamera has a drawback in that the rotation is not simple and renders handling difficult.

SUMMARY OF THE INVENTION

The present invention has been made with a view to resolving the above problem of the prior art, and an essential and principal object of the present invention is to provide an image rotating device for use in a stomatocamera, which enables rotating an image without rotating the stomatocamera frame.

The foregoing and other objects, features and advantages of the present invention will become apparent from the following detailed description and appended claims taken in connection with the accompanying drawings.

DETAILED DESCRIPTION OF THE INVENTION

For attaining the above objects, according to the essential and principal aspect of the present invention, there is provided an image rotating device for use in a stomatocamera, comprising a barrel as a constituent of a stomatocamera frame including a charge coupled device (CCD) and, rotatably built therein, a dope prism.

This image rotating device enables displaying a rotated image on a TV monitor only by revolving the dope prism built in the stomatocamera frame without the need to revolve the camera frame.

In a preferred structure of image rotating device according to the present invention, the dope prism is fixed inside a cylindrical support having a pin erected on its periphery and the support is rotatably fitted in the barrel. The barrel is furnished with a guide channel formed along its circumference, the guide channel adapted to have the pin pierce the guide channel and to allow the pin to move in a circumferential direction. The barrel on its periphery is fitted with an operating ring capable of locking an end of the pin piercing the guide channel and protruding from periphery of the barrel and capable of moving the pin in a circumferential direction.

In this preferred structure, the dope prism built in the camera frame can be rotated by revolving the operating ring fitted to the periphery of the camera frame, so that the image can be rotated without the need to revolve the camera frame.

EFFECT OF THE INVENTION

In the present invention, the stomatocamera is fitted with the rotatably built-in dope prism. Therefore, the observed oral image can be rotated and displayed on the TV monitor without rotating the camera frame.

PREFERRED EMBODIMENT OF THE INVENTION

The present invention will now be described in greater detail with reference to the following Embodiment, which should not be construed as limiting the scope of the invention.

One embodiment of the present invention will be described below with reference to the appended drawings.

Figure 1:
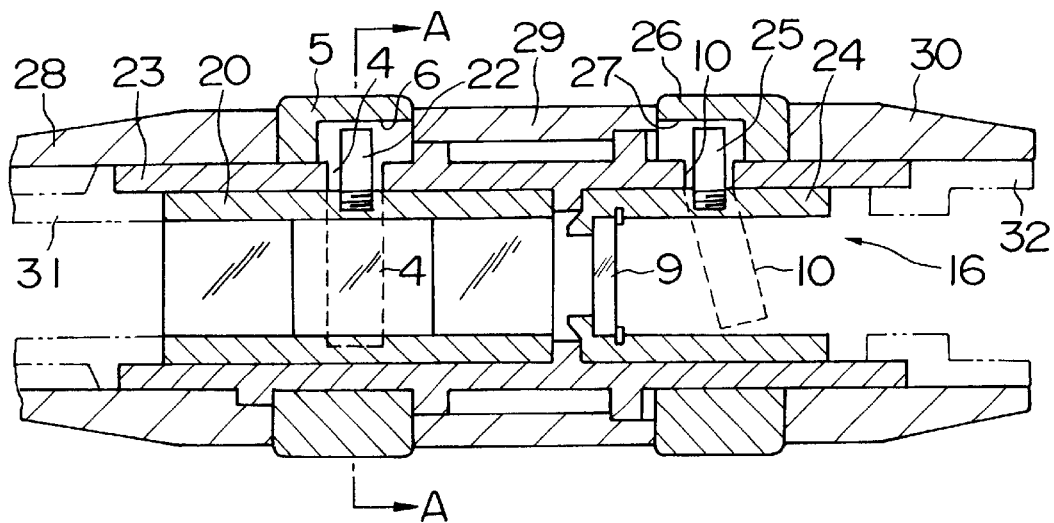
FIG. 1 is a sectional view showing an image rotating mechanism of stomatocamera according to one embodiment of the present invention.
Figure 2A:
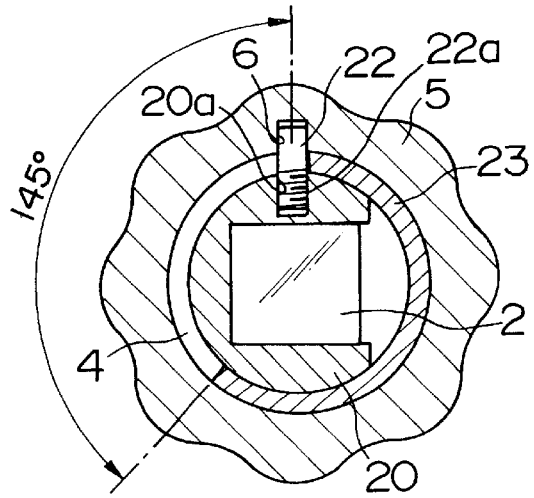
FIG. 2(a) is a section on the line A—A of FIG. 1.
Figure 2B:
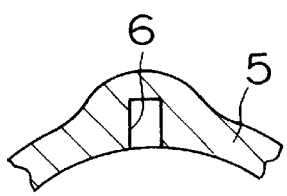
FIG. 2(b) is a partial sectional view of an operating ring.
Figure 3:
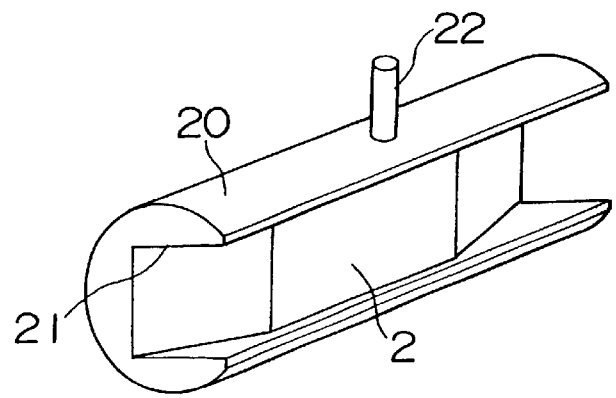
FIG. 3 is a view showing a pin locking channel of rotary ring.
Figure 12:
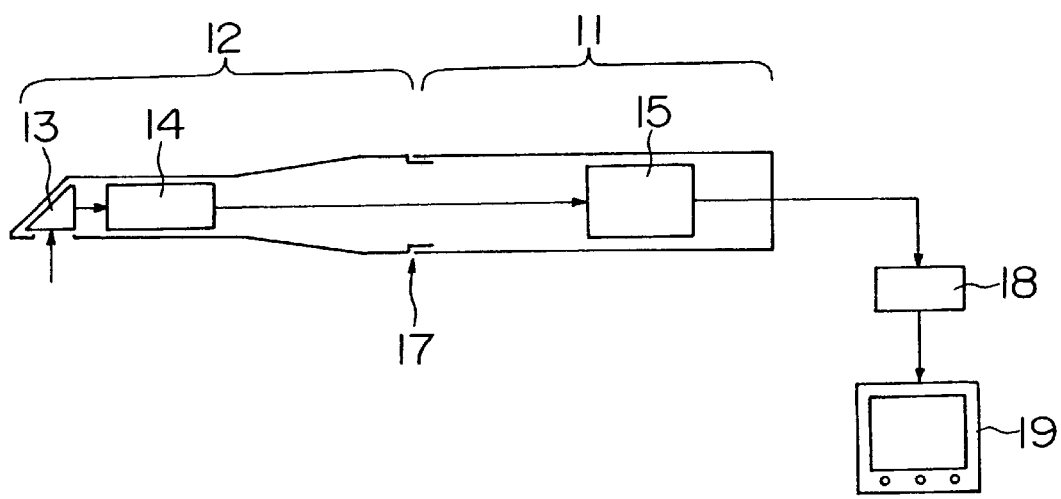
FIG. 12 shows the conventional stomatocamera.
Figure 9:
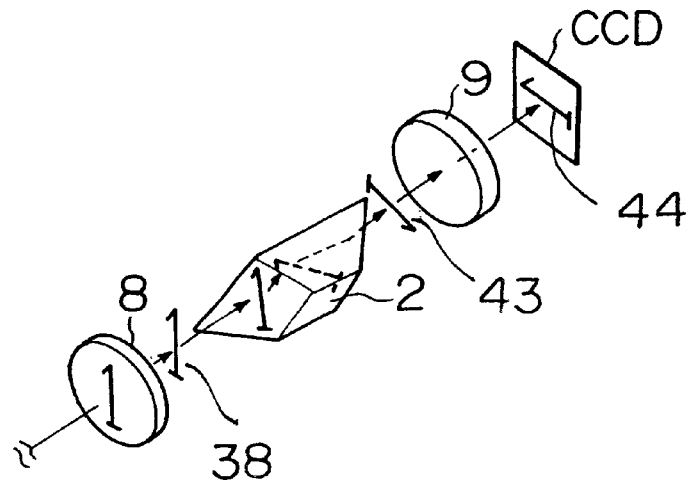
FIG. 9 is a view showing the rotations of an image passing through a first relay lens, a dope prism and a second relay lens.
Figure 10:
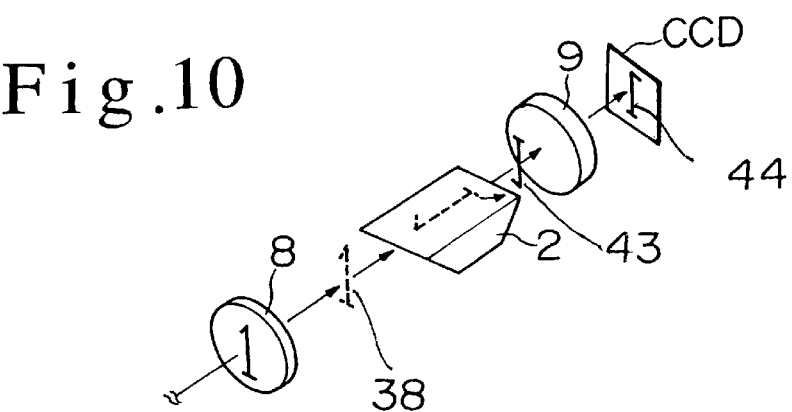
FIG. 10 is a view showing the rotations of an image passing through a first relay lens, a dope prism and a second relay lens.
Figure 11:
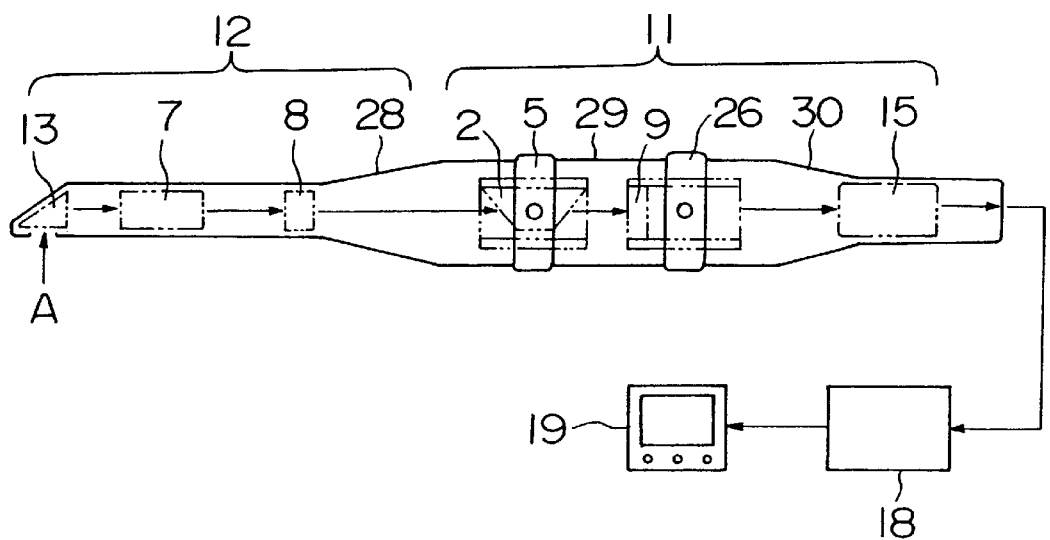
FIG. 11 is a conceptual diagram of the stomatocamera of the present invention.

FIGS. 1 to 11 show one embodiment of the present invention, in which FIG. 1 is a sectional view showing an image rotating mechanism of stomatocamera; FIG. 2(a) is a section on the line A—A of FIG. 1, and FIG. 2(b) is a partial sectional view of an operating ring; FIG. 3 is a view showing a pin locking channel of a rotary ring; FIGS. 4 to 10 are views showing the rotation of an image passing through a lens or lenses; and FIG. 11 is a conceptual diagram of the stomatocamera.

Referring to FIG. 11, in the stomatocamera of the present invention, photographic light A is incident upon rectangular prism 13 disposed in lens unit 12, passes through principal coupling lens 7 and relay lens 8 and reaches dope prism 2 which constitutes an image rotating device. The light is rotated by the dope prism 2 and focused by relay lens 9. The resultant light is subjected to photoelectric transfer by charge coupled device (CCD) 15. The thus produced electrical signal is transmitted to control unit 18. Rotated image is displayed on TV monitor 19.

The dope prism 2 which constitutes an image rotating device has a trapezoidal shape as shown in FIG. 3 and fitted in sideways open ]-shaped channel 21 made in cylindrical support 20. The support 20 has pin 22 erected in its center. Referring to FIG. 2(a), the pin 22 is fixed by fitting screw 22a provided at a lower end of the pin 22 in screw hole 20a of the support 20.

Referring to FIG. 1, the dope prism 2 fitted in the support 20 is rotatably inserted in such a manner that the periphery of the support 20 is fitted in the inner surface of barrel 23 as a constituent of camera frame 11. On the other hand, the barrel 23 is furnished with guide channel 4 arranged in the circumferential direction, which enables moving of the pin 22 within a given angle range (145° in this embodiment) in the circumferential direction, as shown in FIG. 2. The pin 22 is set so as to pierce the guide channel 4 and to protrude from the peripheral surface of the barrel 23.

Head portion of the pin 22 protruding from the peripheral surface of the barrel 23 is locked to cutout 6 (see FIG. 2(b)) of operating ring 5 rotatably fitted to the periphery of the barrel 23 to thereby realize such a construction that the pin 22 can be rotated along the head portion of the guide channel 4 by revolving the operating ring 5 with the pin 22 held in locked condition.

Cylindrical support 24 furnished with relay lens 9 is rotatably fitted to the right side of the barrel 23. The barrel 23 is furnished with focusing device 16 adapted to minutely move the relay lens 9 in the axial direction by rotating operating ring 26 while locking a head portion of pin 25, which pierces channel 10 formed in an oblique direction along the circumference of the barrel 23 and protrudes from the periphery of the barrel 23, to locking channel 27 of the operating ring 26 so as to move the pin 25 in an oblique direction along the channel 10.

The barrel 23 on its side of lens unit 12 is fitted with barrel 31 which is furnished with the built-in rectangular prism 13 and the built-in principal coupling lens 7, and the outer surface thereof is fitted with case 28. On the other hand, the barrel 23 on its side of focusing device 16 is fitted with barrel 32 which is furnished with the built-in charge coupled device, and the outer surface thereof is fitted with case 30. Middle case 29 is interposed between the operating ring 5 and the operating ring 26. Thus, a construction is realized such that the built-in dope prism 2 and focusing device 16 can be rotated by revolving the operating ring 5 and operating ring 26.

The rotation of image performed by the stomatocamera with the above construction will described below.

Figure 4:
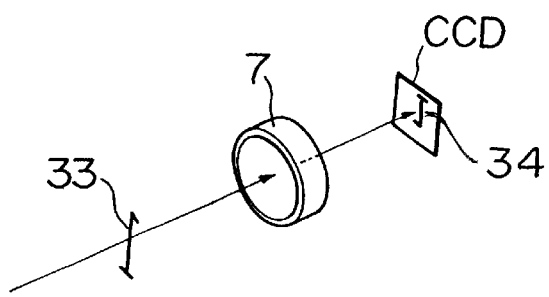
FIG. 4 is a view showing the rotation of an image passing through a principal coupling lens.

FIG. 4 shows the common instance using only one principal coupling lens 7, in which image 33 is turned upside down by the principal coupling lens 7 to thereby form an inverted image.

Figure 5:
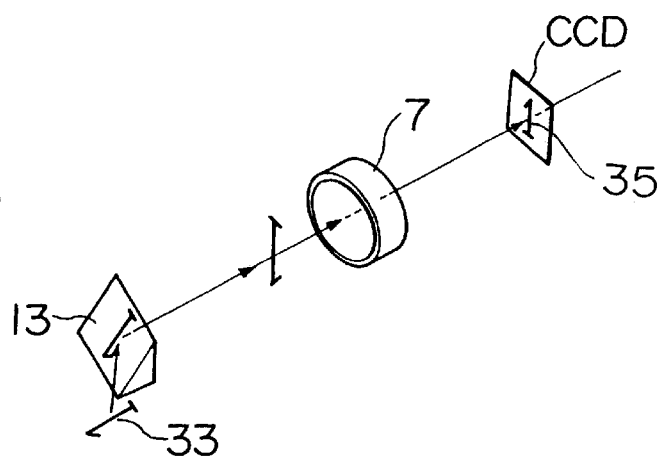
FIG. 5 is a view showing the rotations of an image passing through a rectangular prism and a principal coupling lens.

FIG. 5 shows the common instance using the principal coupling lens 7 in combination with rectangular prism 13, in which image 33 is rolled round backwards and inverted by the rectangular prism 13 and further inverted by the principal coupling lens 7 to thereby form a reversed erect image.

Figure 6:
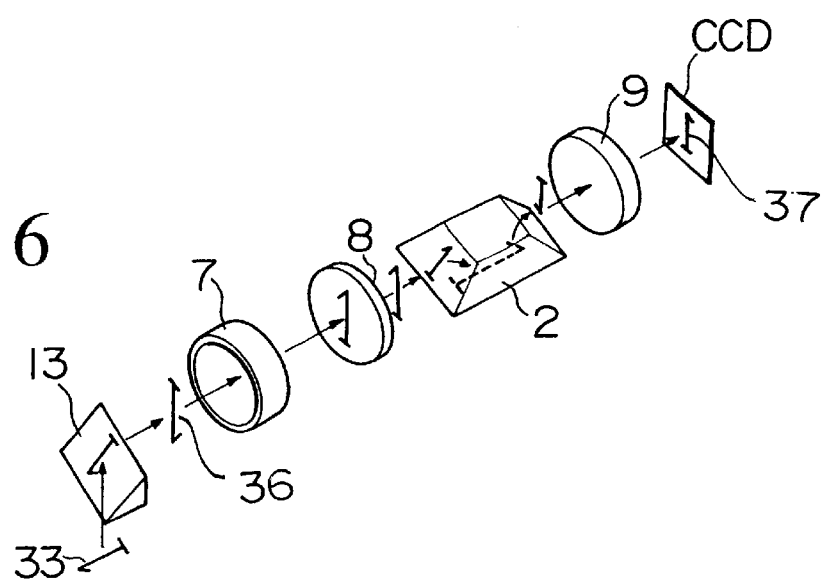
FIG. 6 is a view showing the rotations of an image passing through a rectangular prism, a principal coupling lens, a first relay lens, a dope prism and a second relay lens.

FIG. 6 shows a combination of the rectangular prism 13, the principal coupling lens 7, dope prism 2 and relay lenses 8, 9 arranged in front of and in back of the dope prism 2, in which the dope prism 2 is in an unrotated state. In this combination, image 33 is rolled round and inverted by the rectangular prism 13, further inverted by the principal coupling lens 7, passes as it is through the relay lens 8, rolled round and inverted by the dope prism 2 and still further inverted by the relay lens 9 to thereby form an erect image.

Figure 7:
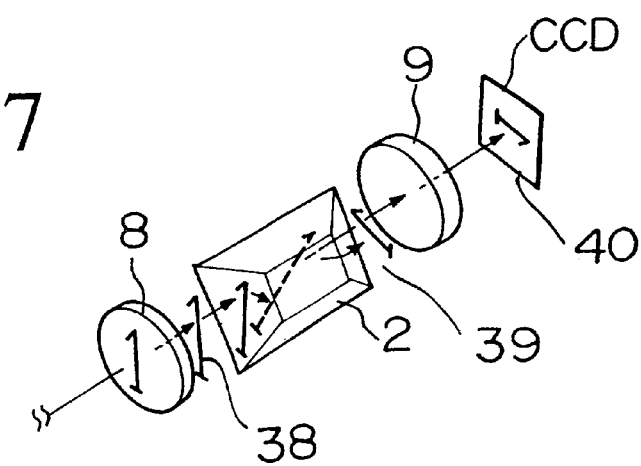
FIG. 7 is a view showing the rotations of an image passing through a first relay lens, a dope prism and a second relay lens.

FIG. 7 shows the same combination as in FIG. 6, except that the dope prism 2 is in a 45° rotated state. The rotation of the dope prism 2 causes the image to rotate in the horizontal direction and reverse to thereby form a leftwards rolled image. The passage thereof through the relay lens 9 produces an opposite rightwards rolled image.

Figure 8:
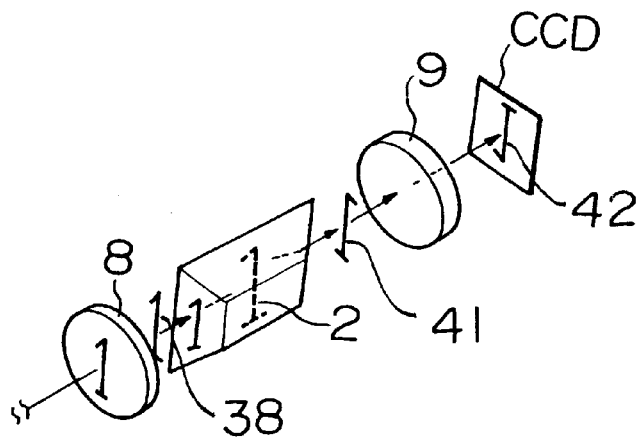
FIG. 8 is a view showing the rotations of an image passing through a first relay lens, a dope prism and a second relay lens.

FIG. 8 shows the same combination as in FIGS. 6–7, except that the dope prism 2 is in a 90° rotated state. The rotation of the dope prism 2 causes the image to reverse to thereby form an erect image. The passage thereof through the relay lens 9 produces an inverted image.

FIG. 9 shows the same combination as in FIGS. 6–8, except that the dope prism 2 is in a 135° rotated state. The rotation of the dope prism 2 forms a reversed and rightwards rolled image, and the passage thereof through the relay lens 9 produces a leftwards rolled image.

FIG. 10 shows the same combination as in FIGS. 6–9, except that the dope prism 2 is in a 180° rotated state, namely, in an overturned state. The rotation of the dope prism 2 forms a rolled round inverted image, and the passage thereof through the relay lens 9 produces an erect image.

FIGS. 6 to 10 illustrate the use of the stomatocamera of the present invention. It is apparent therefrom that an image rotated at an arbitrary angle can be obtained by revolving the dope prism 2 and that a 180° revolution of the dope prism 2 causes the image to undergo one rotation.

With respect to the angle of revolution of the dope prism 2, the range of moving of the pin 22 is limited by the length of the guide channel 4. However, the image can be rotated at a maximum angle of 280° by forming the channel which permits the revolution up to a maximum of 140°. These are practically satisfactory.

What is claimed is:

1. An image rotating device for use in a stomatocamera, said stomatocamera comprising a lens unit fitted with a prism for introducing incident image pickup beams and fitted with a lens for passing the introduced image pickup beams into a camera frame, said camera frame fitted with a built-in charge coupled device for carrying out a photoelectric transfer of the passed image pickup beams to thereby enable observing a given image on a TV monitor, said camera frame including a barrel furnished with a guide channel, said image rotating device comprising a support having a pin erected on its outer surface, said support rotatably fitted in the barrel, and a dope prism fitted in the support, the pin piercing the guide channel of the barrel, said image rotating device further comprising an operating ring rotatably fitted on an outer surface of the barrel, said operating ring having a locking channel wherein an end of the pin of the support is locked, to thereby constitute a rotating mechanism for the dope prism, wherein rotating the operating ring of the rotating mechanism to thereby move the pin of the support along the guide channel of the barrel causes the dope prism fitted in the support to rotate within a given range of angle so that the image observed on the TV monitor can be rotated within a given range of angles.

2. The image rotating device according to claim 1, wherein the lens unit comprises a rectangular prism for introducing incident image pickup beams and a principal coupling lens and relay lens for passing the introduced image pickup beams to the camera frame.

3. The image rotating device according to claim 1, which further comprises a relay lens arranged between the dope prism and the CCD in the camera frame.

4. The image rotating device according to claim 1, which further comprises a relay lens arranged between the dope prism and the CCD in the camera frame and a support having a pin protruding from its outer surface, said support rotatably fitted in the barrel, the barrel furnished with a guide channel, the relay lens fitted in the support, the pin piercing the guide channel of the barrel, said image rotating device further comprising an operating ring rotatably fitted on an outer surface of the barrel, said operating ring having a locking channel wherein an end of the pin of the support is locked, to thereby constitute a regulating mechanism for the relay lens, wherein rotating the operating ring of the regulating mechanism to thereby move the pin of the support along the guide channel of the barrel causes the relay lens fitted in the support to minutely move along optical axis so that focusing can be accomplished.

5. The image rotating device according to claim 3, which further comprises a support having a pin protruding from its outer surface, said support rotatably fitted in the barrel, the barrel furnished with a guide channel, the relay lens fitted in the support, the pin piercing the guide channel of the barrel, said image rotating device further comprising an operating ring rotatably fitted on an outer surface of the barrel, said operating ring having a locking channel wherein an end of the pin of the support is locked, to thereby constitute a regulating mechanism for the relay lens, wherein rotating the operating ring of the regulating mechanism to thereby move the pin of the support along the guide channel of the barrel causes the relay lens fitted in the support to minutely move along optical axis so that focusing can be accomplished.

6. The image rotating device according to claim 2, which further comprises a relay lens arranged between the dope prism and the CCD in the camera frame.

7. The image rotating device according to claim 2, which further comprises a relay lens arranged between the dope prism and the CCD in the camera frame and a support having a pin protruding from its outer surface, said support rotatably fitted in the barrel, the barrel furnished with a guide channel, the relay lens fitted in the support, the pin piercing the guide channel of the barrel, said image rotating device further comprising an operating ring rotatably fitted on an outer surface of the barrel, said operating ring having a locking channel wherein an end of the pin of the support is locked, to thereby constitute a regulating mechanism for the relay lens, wherein rotating the operating ring of the regulating mechanism to thereby move the pin of the support along the guide channel of the barrel causes the relay lens fitted in the support to minutely move along optical axis so that focusing can be accomplished.

8. The image rotating device according to claim 6, which further comprises a support having a pin protruding from its outer surface, said support rotatably fitted in the barrel, the barrel furnished with a guide channel, the relay lens fitted in the support, the pin piercing the guide channel of the barrel, said image rotating device further comprising an operating ring rotatably fitted on an outer surface of the barrel, said operating ring having a locking channel wherein an end of the pin of the support is locked, to thereby constitute a regulating mechanism for the relay lens, wherein rotating the operating ring of the regulating mechanism to thereby move the pin of the support along the guide channel of the barrel causes the relay lens fitted in the support to minutely move along optical axis so that focusing can be accomplished.

* * * * *